United States Patent
Sambursky et al.

(10) Patent No.: US 10,413,587 B2
(45) Date of Patent: *Sep. 17, 2019

(54) HISTATIN FOR CORNEAL WOUND HEALING AND OCULAR SURFACE DISEASE

(71) Applicant: Rapid Pathogen Screening, Inc., Sarasota, FL (US)

(72) Inventors: Robert P. Sambursky, Bradenton, FL (US); Robert W. VanDine, Montoursville, PA (US); Peter Condon, Tierre Verde, FL (US)

(73) Assignee: Rapid Pathogen Screening, Inc., Sarasota, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/180,476

(22) Filed: Jun. 13, 2016

(65) Prior Publication Data

US 2016/0279194 A1 Sep. 29, 2016

Related U.S. Application Data

(63) Continuation of application No. 13/788,803, filed on Mar. 7, 2013, now abandoned.

(60) Provisional application No. 61/648,845, filed on May 18, 2012.

(51) Int. Cl.
  *A61K 9/00* (2006.01)
  *A61K 38/08* (2019.01)
  *A61K 38/10* (2006.01)
  *A61K 38/17* (2006.01)

(52) U.S. Cl.
  CPC ........ *A61K 38/1709* (2013.01); *A61K 9/0048* (2013.01); *A61K 9/0051* (2013.01); *A61K 38/08* (2013.01); *A61K 38/10* (2013.01)

(58) Field of Classification Search
  CPC .... A61K 38/1709; A61K 38/10; A61K 38/08; A61K 9/0048; A61K 9/0051
  See application file for complete search history.

(56) References Cited

U.S. PATENT DOCUMENTS

| | | | |
|---|---|---|---|
| 5,486,503 A | 1/1996 | Oppenheim et al. | |
| 5,631,228 A | 5/1997 | Oppenheim et al. | |
| 5,646,119 A | 7/1997 | Oppenheim et al. | |
| 5,672,351 A | 9/1997 | Chikindas et al. | |
| 5,912,230 A | 6/1999 | Oppenheim et al. | |
| 6,086,863 A | 7/2000 | Ritter et al. | |
| 6,462,070 B1 | 10/2002 | Hasan et al. | |
| 6,555,650 B1 | 4/2003 | Lajoie et al. | |
| 6,833,435 B2 | 12/2004 | Glenn et al. | |
| 7,846,895 B2 | 12/2010 | Eckert et al. | |
| 7,939,501 B2 | 5/2011 | Smith et al. | |
| 2003/0108626 A1 | 6/2003 | Benita et al. | |
| 2006/0222635 A1 | 10/2006 | Centanni et al. | |
| 2009/0143299 A1 | 6/2009 | Schmidtchen et al. | |
| 2010/0173833 A1 | 7/2010 | Lajoie et al. | |
| 2011/0045073 A1 | 2/2011 | Ekhart | |
| 2011/0178010 A1 | 7/2011 | Bolscher et al. | |
| 2013/0310326 A1 | 11/2013 | Sambursky et al. | |

FOREIGN PATENT DOCUMENTS

| | | |
|---|---|---|
| CA | 2285673 A1 | 4/2001 |
| JP | 03261717 A | 11/1991 |
| JP | 04182420 A | 6/1992 |
| JP | 06-234653 A | 8/1994 |
| JP | 06-287146 A | 10/1994 |
| JP | 07258110 A | 10/1995 |
| JP | 2002508390 | 3/2002 |
| WO | 9832427 A1 | 7/1998 |
| WO | 99/31123 | 6/1999 |
| WO | 03079997 A2 | 10/2003 |
| WO | 2008134882 A1 | 11/2008 |
| WO | 2009005798 A2 | 1/2009 |
| WO | 2009087117 A1 | 7/2009 |
| WO | 2012061937 A1 | 5/2012 |

OTHER PUBLICATIONS

"Blepharitis," available at https://web.archive.org/web/20120430004942/http://www.merckmanuals.com/professional/eye_disorders/eyelid_and_lacrimal_disorders/blepharitis.html, 2 pages, Apr. 30, 2012.

"Corneal Transplantation," available at http://web.archive.org/web/20120408220440/http://www.merckmanuals.com/professional/eye_disorders/corneal_disorders/corneal_transplantation.html, 2 pages, Apr. 8, 2012.

"Facts about dry eye," available at https://web.archive.org/web/20120427113628/http://www.nei.nih.gov/health/dryeye/dryeye.asp, 5 pages, Apr. 27, 2012.

"Keratoconjunctivitis Sicca," available at http://www.merckmanuals.com/professional/eye_disorders/corneal_disorders/keratoconjunctivitis_sicca.html, 3 pages, accessed Feb. 2, 2014.

Adessi, et al., "Converting a Peptide into a Drug: Strategies to Improve Stability and Bioavailability," Current Medicinal Chemistry, 2002, 963-978.

(Continued)

*Primary Examiner* — Karlheinz R. Skowronek
*Assistant Examiner* — Li N Komatsu
(74) *Attorney, Agent, or Firm* — Brown & Michaels, PC

(57) ABSTRACT

Histatins may be used for corneal wound healing and as a treatment for ocular surface disease in humans and other animals. For example, histatins could be included in eye drops, eye gels, ointment, glue, or embedded in (polymer) contact lenses.

25 Claims, No Drawings
Specification includes a Sequence Listing.

(56) References Cited

OTHER PUBLICATIONS

Anand-Apte, et al., "Platelet-derived Growth Factor and Fibronectin-stimulated Migration are Differentially Regulated by the Rac and Extracellular Signal-regulated Kinase Pathways," The Journal of Biological Chemistry, 1997, 272, 30688-30692.
Berendsen, "A Glimpse of the Holy Grail?" Science, 1998, 282, 642-643.
Bolscher, et al., "Sortase A as a tool for high-yield histatin cyclization," The FASEB Journal, 2011, vol. 25, 2650-2658.
Bracci, et al., "Synthetic Peptides in the Form of Dendrimers Become Resistant to Protease Activity," J. Biol. Chem., 2003, 278, 46590-46595.
Bradley, et al., "Limits of Cooperativity in a Structurally Modular Protein: Response of the Notch Ankyrin Domain to Analogous Alanine Substitutions in Each Repeat," J. Mol. Biol., 2002, 324, 373-386.
Brand, et al., "Saliva and Wound Healing," The Chinese Journal of Dental Research, 2013, vol. 16, 7-12.
Brewer, et al., "Structure-Based Design of Potent Histatin Analogues," Biochemistry, 2002, vol. 41, 5526-5536.
Cabras, et al., "Tyrosine Polysulfation of Human Salivary Histatin 1. A Post-Translational Modification Specific of the Submandibular Gland," Journal of Proteome Research, 2007, 6, 2472-2480.
Definition of "fragment," http://www.merriam-webster.com/dictionary/fragment, pp. 1-3, accessed May 1, 2014.
Extended European Search Report for European Application No. 13791399.2, dated Dec. 4, 2015.
Gusman, et al., "Salivary Histatin 5 is an Inhibitor of Both Host and Bacterial Enzymes Implicated in Periodontal Disease," Infection and Immunity, Mar. 2001, 1402-1408.
Huang, et al., "Ocular Surface Expression and In Vitro Activity of Antimicrobial Peptides," Current Eye Research, Jan. 2007, 595-609.
International Preliminary Report on Patentability for PCT/EP2009/000241, dated Jul. 13, 2010.
Jumblatt, et al., "MUC7 Expression in the Human Lacrimal Gland and Conjunctiva," Corneal 22(1): 41-45, 2003.
Kavanagh, "Histatins: antimicrobial peptides with therapeutic potential," Journal of Pharmacy and Pharmacology, 2004, 56, 1-5.
Klyce, et al., "Transport processes across the rabbit corneal epithelium: a review," Curr Eye Res, 1985; 4:323-331.
Lu, et al., "UV-Induced Signaling Pathways Associated with Corneal Epithelial Cell Apoptosis," Invest Ophthalmol Vis Sci, 2003; 44: 5102-5109.
McDermott, "Defensins and Other Antimicrobial Peptides at the Ocular Surface," Ocular Surface, 2004, vol. 2, No. 4, 229-247.
Merrifield, "Solid Phase Synthesis," Science, 1986, 341-347.
Murakami, et al., "Histatin as a Synergistic Stimulator with Epidermal Growth Factor of Rabbit Chondrocyte Proliferation," Biochemical and Biophysical Research Communications, 1994, vol. 198, No. 1, 274-280.
Ngo, et al., "Computational Complexity, Protein Structure Prediction, and the Levinthal Paradox," 1994, 491-494.
Nishida, et al., "Fibronectin Enhancement of Corneal Epithelial Wound Healing of Rabbits in Vivo," Arch Ophthalmol, 1984, 102, 455-456.
Oudhoff Thesis, "Discovery of the wound-healing capacity of salivary histatins," Department of Oral Biochemistry of the Academic Centre for Dentistry Amsterdam (ACTA), VU University Amsterdam and University of Amsterdam, The Netherlands, 2010.
Oudhoff, et al., "Histatins are the major wound-closure stimulating factors in human saliva as identified in a cell culture assay," FASEB J, 2008, vol. 22, 3805-3812.
Oudhoff, et al., "Histatins Enhance Wound Closure with Oral and Non-oral Cells," Journal of Dental Research, 2009, vol. 88, 846-850.

Oudhoff, et al., "Structure-activity analysis of histatin, a potent wound healing peptide from human saliva: cyclization of histatin potentiates molar activity 1000-fold," FASEB J, 2009, vol. 23, 3928-3935.
Oudhoff, et al. "The role of salivary histatin and the human cathelicidin LL-37 in wound healing and innate immunity," Bio Chem, 2010, vol. 391, 541-548.
Paulsen, et al. "Intestinal Trefoil Factor/TFF3 Promotes Re-epithelialization of Corneal Wounds," The Journal of Biological Chemistry, 2008, vol. 283, No. 19, 13418-13427.
Perinpanayagam, et al., "Characterization of Low-molecular weight Peptides in Human Parotid Saliva," Journal of Dental Research, 1995, vol. 74, No. 1, 345-350.
Pini, et al., "Characterization of the branched antimicrobial peptide M6 by analyzing its mechanism of action and in vivo toxicity," Journal of Peptide Science, 2007, 13, 393-399.
Reviglio, et al., "Effects of topical nonsteroidal antiinflammatory drugs on the expression of matrix metalloproteinases in the cornea," J Cataract Refract Surg, 2003, 29: 989-997.
Rosler, et al., "Trefoil Factor 3 Is Induced During Degenerative and Inflammatory Joint Disease, Activates Matrix Metalloproteinases, and Enhances Apoptosis of Articular Cartilage Chondrocytes," Arthritis & Rheumatism, 2010, vol. 52, No. 3, 815-825.
Rudinger, "Peptide Hormones," JA Parsons, Ed., 1976, 1-7.
SIGMA, "Designing Custom Peptides," 2004, pp. 1-2, http://www.sigma-genosys.com/peptide_design.asp.
Steele, et al., "Detection of Histatin 5 in Normal Human Schirmer Strip Samples by Mass Spectroscopy," Invest Ophthalmol Vis Sci, 2002, 43, E-Abstract 98.
Sun, et al., "Kinetics of histatin proteolysis in whole saliva and the effect on bioactive domains with metal-binding, antifungal, and wound-healing properties," FASEB J, 2009, vol. 23, 2691-2701.
Teranishi, et al., "Role of Formation of an ERK-FAK-Paxillin Complex in Migration of Human Corneal Epithelial Cells during Wound Closure In Vitro," Investigative Ophthalmology & Visual Science, 2009, 50, 5646-5652.
Troxler, et al., "Structural Relationship between Human Salivary Histatins," Journal of Dental Research, 1990, vol. 69, No. 1, 2-6.
Van't Hof, et al., "Histatins: Multifunctional Salivary Antimicrobial Peptides," Antimicrobial Peptides and Innate Immunity, Progress in Inflammation Research, 2013, 167-181.
Veerman, et al., "Mapping of the Histatin Domain Involved in Cell Migration," The Preliminary Program for IADR General Session, 2010.
Veerman, et al., "Saliva and wound healing," Nederlands tijdschrift voor tandheelkunde, 2011, vol. 118, 253, Summary only.
Voet, et al., "Biochemistry," John Wiley & Sons Inc., 1995, pp. 235-241.
Esparza et al. "Fibronectin Upregulates Gelatinase B (MMP-9) and Induces Coordinated Expression of Gelatinase A (MMP-2) and Its Activator MT1-MMP (MMP-14) by Human T Lymphocyte Cell Lines. A Process Repressed Through RAS/MAP Kinase Signaling Pathways" Blood, vol. 94, No. 8 Oct. 15, 1999: pp. 2754-2766.
Shah et al. "Effects of histatin-1 peptide on human corneal epithelial cells" PLoS ONE 12(5): e0178030. (2017) https://doi.org/10.1371/journal.pone.0178030.
Bukowiecki et al. "Wound-Healing Studies in Cornea and Skin: Parallels, Differences and Opportunities" Int. J. Mol. Sci. 2017, 18, 1257; doi:10.3390/ijms18061257.
Sen et al. "Fibronectin induces matrix metalloproteinase-9 (MMP-9) in human laryngeal carcinoma cells by involving multiple signaling pathways" Biochimie. Oct. 2010; 92(10):1422-34.
Sikorska et al. "Effect of head-to-tail cyclization on conformation of histatin-5" Journal of Peptide Science vol. 20, Issue 12; Dec. 2014.
Håkansson L, et al. "The combined action of hyaluronic acid and fibronectin stimulates neutrophil migration" .J Immunol Oct. 1, 1985, 135 (4) 2735-2739.
Lefebvre et al. "Extra domain A of fibronectin primes leukotriene biosynthesis and stimulates neutrophil migration through activation of Toll-like receptor 4." Arthritis Rheum. Jun. 2011;63(6):1527-33.
De Smet et al. "Human antimicrobial peptides: defensins, cathelicidins and histatins." Biotechnol Lett. Sep. 2005;27(18):1337-4.

(56) References Cited

OTHER PUBLICATIONS

Van Dijk et al. "Human salivary peptide histatin-1 stimulates epithelial and endothelial cell adhesion and barrier function." FASEB J. Sep. 2017;31(9):3922-3933.
Huang et al. "Protective effect of histatin 1 against ultraviolet-induced damage to human corneal epithelial cells " Experimental and Therapeutic Medicine. 2018;15(1):679-684.
Xu Q, et al. "Fibronectin binds insulin-like growth factor-binding protein 5 and abolishes Its ligand-dependent action on cell migration." J Biol Chem. Feb. 6, 2004;279(6):4269-77.
Nishida T, et al. "Peptide therapies for ocular surface disturbances based on fibronectin-integrin interactions." Prog Retin Eye Res. 2015.
Sharma et al. "p38 and ERK1/2 coordinate cellular migration and proliferation in epithelial wound healing: evidence of cross-talk activation between MAP kinase cascades" J Biol Chem. Jun. 13, 2003;278(24):21989-97.
Van Dijk et al. "Histatin-1, a histidine-rich peptide in human saliva, promotes cell-substrate and cell-cell adhesion" FASEB J. Aug. 2015;29(8):3124-32.
Chiquet et al.."Multiple functions of gingival and mucoperiosteal fibroblasts in oral wound healing and repair." Periodontol 2000. Jun. 2015;68(1):21-40.
Koivisto et al. "Integrins in Wound Healing." Advances in Wound Care. 2014;3(12):762-783. doi:10.1089/wound.2013.0436.
Kiribayashi et al. "Angiotensis II induces fibronectin expression in human peritoneal mesothelial cells via ERK 1/2 and p38 MAPK". Kidney International, vol. 67 (2005). pp. 1126-1135.
Nishida et al. "Fibronecting Promotes Epithelial Migration of Cultured Rabbit Cornea in Situ" The Journal of Cell Biology; vol. 97, Nov. 1983.
Grinnell et al. "Distribution of Fibronecting During Wound Healing in Vivo" The Journal of Investigative Dermatology, vol. 76: 181-189, 1981.
Grinnell et al. "Degradation of Fibronectin and Witronectin in Chronic Wound Fluid: Analysis by Cell Blotting, Immunoblotting, and Cell Adhesion Assays" J Invest Dermatol 98: 410-416, 1992.
Torres, et al. The salivary peptide histatin-1 promotes endothelial cell adhesion, migration, and angiogenesis. FASEB J. 31, 4946-4958 (2017).
Torres et al. "Histatins, wound healing, and cell migration." Oral Dieases 2018; 1-11.
Huang et al. "MAP kinases and cell migration." Journal of Cell Science 117, 4619-4628, 2004.
MAPK/ERK in Growth and Differentiation. https://media.cellsignal.com/www/pdfs/science/pathways/MAPK_ERK_Growth.pdf (2003).
Maeng et al. "Role of TGFBIp in Wound Healing and Mucin Expression in Corneal Epithelial Cells". Yonsei Med J 2017; 58(2):423-431.
Lenselink, E. "Role of fibronectin in normal wound healing", International Wound Journal 12:313-316; 2015.
Boink et al. "The Influence of Chronic Wound Extracts on Inflammatory Cytokine and Histatin Stability", PLOS ONE 11(3); Mar. 2016.
Oppenheim et al. "Histatins, a Novel Family of Histidine-rich Proteins in Human Parotid Secretion", The Journal of Biological Chemistry, vol. 263, No. 16 Jun. 5, 1998.
Norris et al. "Salivary metals, age, and gender correlate with cultivable oral Candida carriage levels"; Journal of Microbiology; 2018.
Bugiyama et al. "High-performance liquid chromatographic determination of histatins in human saliva"; Journal of Chromatography; 1993.
ScienceLab.com, "Material Safety Data Sheet"; retrieved from http://www.sciencelab.com/msds.php?msdsId=9927388 downloaded on Aug. 5, 2018.
Khurshid et al. "Oral antimicrobial peptides: Types and role in the oral cavity." Saudi Pharmaceutical Journal. 2016; 24: 515-524. 2016.
Rothstein et al. "Histatin-derived peptides: potential agents to treat localised infections" Expert Opin. Emerging Drugs. 2002; 7(1):47-59. 2002.
Dworecka-Kaszak et al. "High Prevalence of Candida Yeast in Milk Samples from Cows Suffering from Mastitis in Poland" The Scientific World Journal vol. 2012, Article ID 196347. 2012.
Cyclosporine. PubChem. https://pubchem.ncbi.nlm.nih.gov/compound/5284373#section=Top[Nov. 17, 2018 1 :19:37 PM] (Year 2018).

SEQUENCE LISTING

```
<160> NUMBER OF SEQ ID NOS: 33

<210> SEQ ID NO 1
<211> LENGTH: 7
<212> TYPE: PRT
<213> ORGANISM: Artificial sequence
<220> FEATURE:
<223> OTHER INFORMATION: synthetic

<400> SEQUENCE: 1

Ser Asn Tyr Leu Tyr Asp Asn
1               5

<210> SEQ ID NO 2
<211> LENGTH: 9
<212> TYPE: PRT
<213> ORGANISM: Artificial sequence
<220> FEATURE:
<223> OTHER INFORMATION: synthetic

<400> SEQUENCE: 2

Arg Glu Phe Pro Phe Tyr Gly Asp Tyr
1               5

<210> SEQ ID NO 3
<211> LENGTH: 6
<212> TYPE: PRT
<213> ORGANISM: Artificial sequence
<220> FEATURE:
<223> OTHER INFORMATION: synthetic

<400> SEQUENCE: 3

Glu Lys His His Ser His
1               5

<210> SEQ ID NO 4
<211> LENGTH: 38
<212> TYPE: PRT
<213> ORGANISM: Artificial sequence
<220> FEATURE:
<223> OTHER INFORMATION: synthetic

<400> SEQUENCE: 4

Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30
```

```
Asn Tyr Leu Tyr Asp Asn
            35

<210> SEQ ID NO 5
<211> LENGTH: 27
<212> TYPE: PRT
<213> ORGANISM: Artificial sequence
<220> FEATURE:
<223> OTHER INFORMATION: synthetic

<400> SEQUENCE: 5

Arg Lys Phe His Glu Lys His His Ser His Arg Glu Phe Pro Phe Tyr
1               5                   10                  15

Gly Asp Tyr Gly Ser Asn Tyr Leu Tyr Asp Asn
            20                  25

<210> SEQ ID NO 6
<211> LENGTH: 32
<212> TYPE: PRT
<213> ORGANISM: Artificial sequence
<220> FEATURE:
<223> OTHER INFORMATION: synthetic

<400> SEQUENCE: 6

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 7
<211> LENGTH: 15
<212> TYPE: PRT
<213> ORGANISM: Artificial sequence
<220> FEATURE:
<223> OTHER INFORMATION: synthetic

<400> SEQUENCE: 7

Glu Lys His His Ser His Arg Glu Phe Pro Phe Tyr Gly Asp Tyr
1               5                   10                  15

<210> SEQ ID NO 8
<211> LENGTH: 17
<212> TYPE: PRT
<213> ORGANISM: Artificial sequence
<220> FEATURE:
<223> OTHER INFORMATION: synthetic

<400> SEQUENCE: 8

Arg Glu Phe Pro Phe Tyr Gly Asp Tyr Gly Ser Asn Tyr Leu Tyr Asp
1               5                   10                  15

Asn

<210> SEQ ID NO 9
<211> LENGTH: 19
<212> TYPE: PRT
<213> ORGANISM: Artificial sequence
<220> FEATURE:
<223> OTHER INFORMATION: synthetic

<400> SEQUENCE: 9

Ser His Arg Glu Phe Pro Phe Tyr Gly Asp Tyr Gly Ser Asn Tyr Leu
1               5                   10                  15

Tyr Asp Asn
```

<210> SEQ ID NO 10
<211> LENGTH: 21
<212> TYPE: PRT
<213> ORGANISM: Artificial sequence
<220> FEATURE:
<223> OTHER INFORMATION: synthetic

<400> SEQUENCE: 10

His His Ser His Arg Glu Phe Pro Phe Tyr Gly Asp Tyr Gly Ser Asn
1               5                   10                  15

Tyr Leu Tyr Asp Asn
            20

<210> SEQ ID NO 11
<211> LENGTH: 23
<212> TYPE: PRT
<213> ORGANISM: Artificial sequence
<220> FEATURE:
<223> OTHER INFORMATION: synthetic

<400> SEQUENCE: 11

Glu Lys His His Ser His Arg Glu Phe Pro Phe Tyr Gly Asp Tyr Gly
1               5                   10                  15

Ser Asn Tyr Leu Tyr Asp Asn
            20

<210> SEQ ID NO 12
<211> LENGTH: 25
<212> TYPE: PRT
<213> ORGANISM: Artificial sequence
<220> FEATURE:
<223> OTHER INFORMATION: synthetic

<400> SEQUENCE: 12

Phe His Glu Lys His His Ser His Arg Glu Phe Pro Phe Tyr Gly Asp
1               5                   10                  15

Tyr Gly Ser Asn Tyr Leu Tyr Asp Asn
            20                  25

<210> SEQ ID NO 13
<211> LENGTH: 19
<212> TYPE: PRT
<213> ORGANISM: Artificial sequence
<220> FEATURE:
<223> OTHER INFORMATION: synthetic

<400> SEQUENCE: 13

Arg Lys Phe His Glu Lys His His Ser His Arg Glu Phe Pro Phe Tyr
1               5                   10                  15

Gly Asp Tyr

<210> SEQ ID NO 14
<211> LENGTH: 15
<212> TYPE: PRT
<213> ORGANISM: Artificial sequence
<220> FEATURE:
<223> OTHER INFORMATION: synthetic

<400> SEQUENCE: 14

Glu Lys His His Ser His Arg Glu Phe Pro Phe Tyr Gly Asp Tyr
1               5                   10                  15

<210> SEQ ID NO 15
<211> LENGTH: 21
<212> TYPE: PRT

<213> ORGANISM: Artificial sequence
<220> FEATURE:
<223> OTHER INFORMATION: synthetic

<400> SEQUENCE: 15

Arg Lys Phe His Glu Lys His His Ser His Arg Glu Phe Pro Phe Tyr
1               5                   10                  15

Gly Asp Tyr Gly Ser
            20

<210> SEQ ID NO 16
<211> LENGTH: 17
<212> TYPE: PRT
<213> ORGANISM: Artificial sequence
<220> FEATURE:
<223> OTHER INFORMATION: synthetic

<400> SEQUENCE: 16

Glu Lys His His Ser His Arg Glu Phe Pro Phe Tyr Gly Asp Tyr Gly
1               5                   10                  15

Ser

<210> SEQ ID NO 17
<211> LENGTH: 23
<212> TYPE: PRT
<213> ORGANISM: Artificial sequence
<220> FEATURE:
<223> OTHER INFORMATION: synthetic

<400> SEQUENCE: 17

Arg Lys Phe His Glu Lys His His Ser His Arg Glu Phe Pro Phe Tyr
1               5                   10                  15

Gly Asp Tyr Gly Ser Asn Tyr
            20

<210> SEQ ID NO 18
<211> LENGTH: 19
<212> TYPE: PRT
<213> ORGANISM: Artificial sequence
<220> FEATURE:
<223> OTHER INFORMATION: synthetic

<400> SEQUENCE: 18

Glu Lys His His Ser His Arg Glu Phe Pro Phe Tyr Gly Asp Tyr Gly
1               5                   10                  15

Ser Asn Tyr

<210> SEQ ID NO 19
<211> LENGTH: 25
<212> TYPE: PRT
<213> ORGANISM: Artificial sequence
<220> FEATURE:
<223> OTHER INFORMATION: synthetic

<400> SEQUENCE: 19

Arg Lys Phe His Glu Lys His His Ser His Arg Glu Phe Pro Phe Tyr
1               5                   10                  15

Gly Asp Tyr Gly Ser Asn Tyr Leu Tyr
            20                  25

<210> SEQ ID NO 20
<211> LENGTH: 21
<212> TYPE: PRT
<213> ORGANISM: Artificial sequence

```
<220> FEATURE:
<223> OTHER INFORMATION: synthetic

<400> SEQUENCE: 20

Glu Lys His His Ser His Arg Glu Phe Pro Phe Tyr Gly Asp Tyr Gly
1               5                   10                  15

Ser Asn Tyr Leu Tyr
            20

<210> SEQ ID NO 21
<211> LENGTH: 17
<212> TYPE: PRT
<213> ORGANISM: Artificial sequence
<220> FEATURE:
<223> OTHER INFORMATION: synthetic

<400> SEQUENCE: 21

Arg Lys Phe His Glu Lys His His Ser His Arg Glu Phe Pro Phe Tyr
1               5                   10                  15

Gly

<210> SEQ ID NO 22
<211> LENGTH: 13
<212> TYPE: PRT
<213> ORGANISM: Artificial sequence
<220> FEATURE:
<223> OTHER INFORMATION: synthetic

<400> SEQUENCE: 22

Glu Lys His His Ser His Arg Glu Phe Pro Phe Tyr Gly
1               5                   10

<210> SEQ ID NO 23
<211> LENGTH: 19
<212> TYPE: PRT
<213> ORGANISM: Artificial sequence
<220> FEATURE:
<223> OTHER INFORMATION: synthetic

<400> SEQUENCE: 23

His His Ser His Arg Glu Phe Pro Phe Tyr Gly Asp Tyr Gly Ser Asn
1               5                   10                  15

Tyr Leu Tyr

<210> SEQ ID NO 24
<211> LENGTH: 17
<212> TYPE: PRT
<213> ORGANISM: Artificial sequence
<220> FEATURE:
<223> OTHER INFORMATION: synthetic

<400> SEQUENCE: 24

Ser His Arg Glu Phe Pro Phe Tyr Gly Asp Tyr Gly Ser Asn Tyr Leu
1               5                   10                  15

Tyr

<210> SEQ ID NO 25
<211> LENGTH: 15
<212> TYPE: PRT
<213> ORGANISM: Artificial sequence
<220> FEATURE:
<223> OTHER INFORMATION: synthetic

<400> SEQUENCE: 25
```

Ser His Arg Glu Phe Pro Phe Tyr Gly Asp Tyr Gly Ser Asn Tyr
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: synthetic

<400> SEQUENCE: 26

Phe Pro Phe Tyr Gly Asp Tyr Gly Ser Asn Tyr Leu Tyr Asp Asn
1               5                   10                  15

<210> SEQ ID NO 27
<211> LENGTH: 13
<212> TYPE: PRT
<213> ORGANISM: Artificial sequence
<220> FEATURE:
<223> OTHER INFORMATION: synthetic

<400> SEQUENCE: 27

Phe Tyr Gly Asp Tyr Gly Ser Asn Tyr Leu Tyr Asp Asn
1               5                   10

<210> SEQ ID NO 28
<211> LENGTH: 15
<212> TYPE: PRT
<213> ORGANISM: Artificial sequence
<220> FEATURE:
<223> OTHER INFORMATION: synthetic

<400> SEQUENCE: 28

His His Ser His Arg Glu Phe Pro Phe Tyr Gly Asp Tyr Gly Ser
1               5                   10                  15

<210> SEQ ID NO 29
<211> LENGTH: 13
<212> TYPE: PRT
<213> ORGANISM: Artificial sequence
<220> FEATURE:
<223> OTHER INFORMATION: synthetic

<400> SEQUENCE: 29

Ser His Arg Glu Phe Pro Phe Tyr Gly Asp Tyr Gly Ser
1               5                   10

<210> SEQ ID NO 30
<211> LENGTH: 24
<212> TYPE: PRT
<213> ORGANISM: Artificial sequence
<220> FEATURE:
<223> OTHER INFORMATION: synthetic

<400> SEQUENCE: 30

Asp Ser His Ala Lys Arg His His Gly Tyr Lys Arg Lys Phe His Glu
1               5                   10                  15

Lys His His Ser His Arg Gly Tyr
            20

<210> SEQ ID NO 31
<211> LENGTH: 14
<212> TYPE: PRT
<213> ORGANISM: Artificial sequence
<220> FEATURE:
<223> OTHER INFORMATION: synthetic

```
-continued

<400> SEQUENCE: 31

Gly Tyr Lys Arg Lys Phe His Glu Lys His His Ser His Arg
1               5                   10

<210> SEQ ID NO 32
<211> LENGTH: 11
<212> TYPE: PRT
<213> ORGANISM: Artificial sequence
<220> FEATURE:
<223> OTHER INFORMATION: synthetic

<400> SEQUENCE: 32

Ser His Arg Glu Phe Pro Phe Tyr Gly Asp Tyr
1               5                   10

<210> SEQ ID NO 33
<211> LENGTH: 44
<212> TYPE: PRT
<213> ORGANISM: Artificial sequence
<220> FEATURE:
<223> OTHER INFORMATION: synthetic

<400> SEQUENCE: 33

Gly Gly Asp Ser His Glu Lys Arg His His Gly Tyr Arg Arg Lys Phe
1               5                   10                  15

His Glu Lys His His Ser His Arg Glu Phe Pro Phe Tyr Gly Asp Tyr
            20                  25                  30

Gly Ser Asn Tyr Leu Tyr Asp Asn Leu Pro Glu Thr
            35                  40
```

HISTATIN FOR CORNEAL WOUND HEALING AND OCULAR SURFACE DISEASE

REFERENCE TO RELATED APPLICATIONS

This is a continuation application of application Ser. No. 13/788,803, filed Mar. 7, 2013, entitled "HISTATIN FOR CORNEAL WOUND HEALING AND OCULAR SURFACE DISEASE", which is now abandoned and which claims one or more inventions which were disclosed in Provisional Application No. 61/648,845, filed May 18, 2012, entitled "HISTATIN FOR CORNEAL WOUND HEALING AND OCULAR SURFACE DISEASE". The benefit under 35 USC § 119(e) of the United States provisional application is hereby claimed, and the aforementioned applications are hereby incorporated herein by reference.

BACKGROUND OF THE INVENTION

Field of the Invention

The invention pertains to the field of wound and disease healing. More particularly, the invention pertains to corneal wound healing and treating ocular surface disease using histatins.

Description of Related Art

Histatins have been shown in in vitro studies to be wound healing agents from saliva. More specifically, WO 2009/087117 (and its U.S. equivalent U.S. Patent Publication 2011/0178010), herein incorporated by reference, identified peptides of histatin, which had wound healing properties in vitro.

Histatin 1 (Hst-1) and Histatin 2 (Hst-2) have been identified as major wound-closing factors in human saliva ("Discovery of the Wound Healing Capacity of Salivary Histatins", thesis of Menno Johannes Oudhoff, Academic Centre for Dentistry Amsterdam (ACTA), VU University Amsterdam and University of Amsterdam, The Netherlands, 2010, herein incorporated by reference). These studies were all done in vitro and can not be translated to a finding for therapeutic or clinical use, especially since wound and disease healing are complex processes that need to be highly regulated in order to function properly.

SUMMARY OF THE INVENTION

Histatins may be used for corneal wound healing and as a treatment for ocular surface disease in humans and other animals. For example, histatins could be included in eye drops, eye gels, ointment, glue, or embedded in (polymer) contact lenses.

In one preferred embodiment, a method of treating corneal wounds includes the step of administering a therapeutic amount of at least a peptide fragment of a histatin at a site of a corneal wound. The histatin is preferably administered using eye drops, gels, ointments including histatin, tissue glue, or by incorporating histatin into a contact lens worn by a patient. In a preferred embodiment, the therapeutic amount of histatin accelerates wound healing compared to corneal wounds not treated with histatin. The peptide fragment of the histatin preferably includes a sequence selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; and any combination of SEQ ID NO: 1 through SEQ ID NO: 33.

In some preferred embodiments, the histatin includes a) at least a peptide fragment of histatin 5 and b) at least a peptide fragment of histatin 1, at least a peptide fragment of histatin 2 or a combination of at least a peptide fragment of histatin 1 and at least a peptide fragment of histatin 2. In other preferred embodiments, the histatin is at least a peptide fragment of histatin 1, at least a peptide fragment of histatin 2, at least a peptide fragment of histatin 5, or any combination of a peptide fragment of histatin 1, a peptide fragment of histatin 2 and a peptide fragment of histatin 5.

In other preferred embodiments, the histatin is histatin 1 (SEQ ID NO: 4), histatin 2 (SEQ ID NO: 5), histatin 5 (SEQ ID NO: 30), or any combination of histatin 1, histatin 2, and histatin 5. In other preferred embodiments, the histatin includes a) histatin 5 (SEQ ID NO: 30) and b) histatin 1 (SEQ ID NO: 4), histatin 2 (SEQ ID NO: 5), or a combination of histatin 1 and histatin 2.

In another preferred embodiment, a therapeutic amount of at least a peptide fragment of a histatin is administered to an ocular surface to treat ocular surface disease. The histatin is preferably administered using eye drops, gels, ointments including histatin, tissue glue, or by incorporating histatin into a contact lens worn by a patient. In a preferred embodiment, the therapeutic amount of histatin accelerates healing of ocular surface disease compared to ocular surface disease not treated with histatin. The peptide fragment of the histatin preferably includes a sequence selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; and any combination of SEQ ID NO: 1 through SEQ ID NO: 33.

In some preferred embodiments, the histatin includes a) at least a peptide fragment of histatin 5 and b) at least a peptide fragment of histatin 1, at least a peptide fragment of histatin 2 or a combination of at least a peptide fragment of histatin 1. In other preferred embodiments, the histatin is at least a peptide fragment of histatin 1, at least a peptide fragment of histatin 2, at least a peptide fragment of histatin 5 or any combination of a peptide fragment of histatin 1, a peptide fragment of histatin 2 and a peptide fragment of histatin 5.

In other preferred embodiments, the histatin is histatin 1 (SEQ ID NO: 4), histatin 2 (SEQ ID NO: 5), histatin 5 (SEQ ID NO: 30), or any combination of histatin 1, histatin 2, and histatin 5. In other preferred embodiments the histatin includes a) histatin 5 (SEQ ID NO: 30) and b) histatin 1 (SEQ ID NO: 4), histatin 2 (SEQ ID NO: 5), or a combination of histatin 1 and histatin 2.

DETAILED DESCRIPTION OF THE INVENTION

Histatins are naturally occurring oral peptides produced by humans and non-human primates that demonstrate direct anti-infective activity, potent anti-inflammatory properties, and stimulate epithelial wound healing in several tissue and organ culture systems. A research facility has developed a technique to isolate this natural substance, making it a potential topical treatment for wounds.

In a preferred embodiment, a peptide including at least one amino acid sequence of at least eight amino acids adjacently present in Histatin 1, 2, 3, and/or 5 is used to treat a corneal wound or ocular surface disease.

In one preferred embodiment, a method of treating corneal wounds includes the step of administering a therapeutic amount of at least a portion of a histatin peptide at a site of a corneal wound. In another preferred embodiment, a method of treating ocular surface disease includes the step of administering a therapeutic amount of at least a portion of a histatin peptide to an ocular surface. The ocular surface diseases may include, but are not limited to, dry eyes, corneal ulcerations and erosions, inflammatory and infectious keratitis and conjunctivitis, surgical interventions, and trauma.

The histatin is preferably administered using eye drops, gels, ointments including histatin, tissue glue, or by incorporating histatin into a contact lens worn by a patient. In a preferred embodiment, the therapeutic amount of histatin accelerates wound or ocular surface disease healing compared to corneal wounds or ocular surface diseases not treated with histatin.

In some preferred embodiments, the histatin concentration is between approximately 0.1 µg/ml and approximately 1000 mg/ml. In other preferred embodiments, the histatin concentration is between approximately 0.1 µg/ml and 10 µg/ml. In some preferred embodiments, the histatin concentration is greater than or equal to approximately 1 µM.

The administering step may be repeated multiple times per day and/or for a plurality of days. In one preferred embodiment, this step is repeated at least one time a day for a plurality of days. In another preferred embodiment, the step is repeated chronically at least one time a day. In some preferred embodiments, the step is repeated up to hourly for a plurality of days. In another preferred embodiment, the step is repeated at least two times a day for a plurality of days. In yet another preferred embodiment, the step is repeated at least three times a day for a plurality of days, for example for seven days. In another preferred embodiment, the step is repeated four times a day for five days.

In one preferred embodiment, the histatin is a peptide including 8 to 44 amino acids. In some preferred embodiments, the peptide is a L-peptide. In other preferred embodiments, the peptide is a cyclic peptide.

In some preferred embodiments, the amino acid sequence of the histatin peptide is one or more of SEQ ID NOS: 1 through 33, or any combinations of these sequences. In alternative embodiments, one or more of the amino acid sequences have a substitution, deletion and/or insertion of up to 3 amino acids. In other alternative embodiments, one or more of the amino acid sequences have a substitution, a deletion and/or an insertion of two or less amino acids. In other alternative embodiments, one or more of the amino acid sequences have a substitution, a deletion, and/or an insertion in one amino acid.

The SEQ ID NO: 4 peptide is also known as Histatin 1 (Hst-1). Note that the first serine in this amino acid sequence may be a phosphoserine. The SEQ ID NO: 5 peptide is also known as Histatin 2 (Hst-2, also equivalent to amino acids 12-38 of Hst-1). The SEQ ID NO: 6 peptide is also known as Histatin 3 (Hst-3). The SEQ ID NO: 30 peptide is also known as Histatin 5 (Hst-5). Parts and fragments of each of these amino acid sequences may be used, alone or in combination, including but not limited to SEQ ID NOS: 1-3, 7-29 (for Histatin 1, Histatin 2 and Histatin 3) and SEQ ID NO: 31 (for Histatin 5) to facilitate wound closure in the embodiments described herein. While the L stereoisomer of the amino acids is preferred for the amino acid sequences described herein, D stereoisomers may alternatively be used. Alternatively, amino acid sequences that include these histatins and other amino acids, for example SEQ ID NO: 33, which is a sortase cyclized histatin (including all of Histatin 1), may be used in the embodiments described herein. Any histatin sequences could be cyclized and used in the embodiments described herein.

Some preferred embodiments use amino acid sequences from Hst-1 and/or Hst-2 in combination with amino acid sequences from Hst-5 to treat corneal wounds or ocular surface disease. In these embodiments, one or more amino acid sequences from Hst-1 and/or Hst-2 are chosen, and one or more amino acid sequences from Hst-5 are chosen. In some embodiments, the full length Histatin 1 (SEQ ID NO: 4), full length Histatin 2 (SEQ ID NO: 5), and/or the full length Histatin 5 (SEQ ID NO: 30) could be used. In other embodiments, portions of Hst-1, Hst-2, and/or Hst-5 could be used. For example, SEQ ID NO: 29, which is equivalent to amino acids 20-32 of Histatin 1, may be a preferred amino acid sequence to use for wound closure in some embodiments. In other examples, peptides including SEQ ID NO: 32, a peptide fragment of Histatin 1 and Histatin 2 that appears to be a core motif for wound closure, may be used. Other preferred sequences from Hst-1 and Hst-2 include, but are not limited to, SEQ ID NO: 8, SEQ ID NO: 9 and SEQ ID NO: 13. As another example, SEQ ID NO: 31, a fragment of Histatin 5 (Gusman et al., "Salivary Histatin 5 is an inhibitor ob Both Host and Bacterial Enzymes Implicated in Periodontal Disease", Infect. Immun 2001, 69(3): 1402, pp. 1402-1408, herein incorporated by reference), may be used, preferably in combination with Histatin 1 or Histatin 2 or fragments thereof. In other preferred embodiments, fragments of Hst-1 or Hst-2 are used with full length Hst-5 (SEQ ID NO: 30) or full length Hst-1 (SEQ ID NO: 4) or Hst-2 (SEQ ID NO: 5) are used with fragments of Hst-5 (for example, SEQ ID NO: 31). In yet other embodiments, any combination of fragments of Hst-1 and/or Hst-2, full length Hst-1 and/or Hst-2, fragments of Hst-5, or full length Hst-5 may be used. In some preferred embodiments, the concentration of the Hst-5 peptide used is greater than or equal to approximately 1 µM.

The amino acids and the peptides described herein may include at least one functional grouping (for example, an amine and/or carboxylic group) protected with a protective grouping in some embodiments. Since the peptides are applied to tissue, skin or a wound, a protected form of the peptide may be preferred to resist degradation. The form of protection needs to be biologically compatible and compatible with pharmaceutical use. Some examples include, but are not limited to, the acylation or the acetylation of the amino-terminal ends, cyclization or the amidation or the esterfication of the carboxy-terminal ends. Thus, the peptides described herein may be used in a protected form.

The peptides described herein may be made by traditional chemical synthesis, enzymatic synthesis, or any other method known in the art.

The peptides preferably include at least 8 amino acids. In one preferred embodiment, the peptides include a range of 8 to 44 amino acids, but the peptides may alternatively include more than 44 amino acids.

In Vivo Studies

Efficacy studies of histatin for corneal wound healing utilize an animal model, namely rabbits. Histatins are naturally produced substances that stimulate healing in several tissue and organ culture systems. The results of these studies demonstrate that histatin has a significant dose dependent accelerated healing activity for corneal wounds.

Ocular surface disorders including, but not limited to, dry eyes, conical ulcerations and erosions, inflammatory and infectious keratitis and conjunctivitis, surgical interventions, and trauma all lead to disruptions in the integrity of the conical and conjunctival cellular barrier that result in increased risk of infection, pain, and reduced visual acuity. Histatins have a potential use in the treatment of ocular surface trauma/injury and infectious disease.

The outer layer of the cornea, the corneal epithelium, serves as a physical barrier against the environment and thus also as a line of defense to prevent infectious and/or toxic agents from infecting/affecting the tissue. When injury occurs to the surface of the cornea, the corneal epithelium spearheads a wound healing process (see, for example, Klyce S D, Crosson C E. "Transport processes across the rabbit conical epithelium: a review". Curr Eye Res. 1985; 4:323-331 and Lu L, Wang L, Shell B. "UV-induced signaling pathways associated with corneal epithelial cell apoptosis". Invest Ophthalmol Vis Sci. 2003; 44:5102-5109, both herein incorporated by reference).

The study disclosed herein evaluates and quantifies the wound healing effects of histatins on the ocular surface of New Zealand White rabbits.

Brief Methodology

Epithelial defects are created in the right eye (oculus dexter, OD) of 12 New Zealand White rabbits. Due to animal regulations, bilateral wounding is not permitted. After the epithelial defects are made, the rabbits are randomized into treatment groups. Two (2) groups are treated with different cyclized histatin concentrations: 0.1 µg/ml and 10 µg/ml dissolved into an ophthalmic artificial tear preparation and delivered to the rabbits as an eye drop three times daily. Histatins known in the art, including, but not limited to, amino acid SEQ ID NOS: 1 through 33, which include Hst-1 (SEQ ID NO: 4), Hst-2 (SEQ ID NO: 5), Hst-3 (SEQ ID NO: 6), Hst-5 (SEQ ID NO: 30), and sortase cyclized histatin (SEQ ID NO: 33), may be used in these studies or in treatment protocols. One (1) group is treated with an inactive/inert formulation (control). This control group should receive the same vehicle identical to the other two groups but without histatin. An over-the-counter artificial tear preferably serves as the vehicle. The initial study included four (4) animals/group in three (3) groups, for a total of twelve rabbits.

The groups are to be treated with agent (either histatin or an inactive/inert formulation of artificial tears) three times/day (TID) for 7 days. Each rabbit group is preferably given moxifloxicin treatment to prevent infection.

The corneal wounds are then evaluated daily for the corneal wound healing abilities of histatin via fluorescein staining, fluorescent slit lamp biomicrophotography and computerized area determination. Evaluators are masked to the therapeutic treatment given to the rabbits. After healing, two (2) animals from each group are euthanized, and the corneas collected for histological processing (H&E staining with subsequent evaluation by veterinary histopathologist). The decision to perform histopathologic analysis after tissue procurement is made only if there is proven difference in healing between the different treatment groups and the controls. At study termination (study preferably continues for seven days), the remaining animals are euthanized.

Results

The data from a first study using the methodology above is shown in Table 1. The histatin used in this study was cyclized histatin 1. The histatin 1 used was a sortase cyclized histatin with amino acid SEQ ID NO: 33, in which the "C-terminal" T is linked to the "N-terminal" G. Table 2 shows the mm size values (without the standard deviation) as an approximate percentage of the size at 1 hour post wound for each of the three groups. Pathological analysis of the rabbit corneas showed no toxicity.

TABLE 1

| Hours Post Wound | Control ($mm^2$) | 0.1 µg/ml ($mm^2$) | 10 µg/ml ($mm^2$) |
|---|---|---|---|
| 0 | 69.3 ± 17.3 | 112.7 ± 37.8 | 88.4 ± 31.6 |
| 6 | 72.6 ± 15.2 | 96.2 ± 13.6 | 74.0 ± 14.7 |
| 24 | 50.6 ± 16.2 | 77.5 ± 25.0 | 51.4 ± 9.3 |
| 30 | 46.6 ± 25.8 | 48.8 ± 8.0 | 37.7 ± 9.4 |
| 48 | 13.6 ± 20.2 | 2.7 ± 3.1 | 0.00 ± 0.07 |
| 54 | 5.2 ± 7.9 | 0.00 ± 0.00 | 0.00 ± 0.00 |
| 72 | 0.00 ± 0.00 | 0.00 ± 0.00 | 0.00 ± 0.00 |

TABLE 2

| Hours Post Wound | Control- Percentage of 1 hour post wound size | 0.1 ug/ml- Percentage of 1 hour post wound size | 10 ug/ml- Percentage of 1 hour post wound size |
|---|---|---|---|
| 0 | 100% | 100% | 100% |
| 6 | 105% | 85% | 84% |
| 24 | 73% | 69% | 58% |
| 30 | 67% | 43% | 43% |
| 48 | 20% | 2% | 0% |
| 54 | 8% | 0% | 0% |
| 72 | 0% | 0% | 0% |

The results above show that histatin demonstrates a significant dose dependent accelerated healing activity of corneal wounds. While Table 2 does not take into account the standard deviations from Table 1, the percentages clearly indicate that the wounds treated with 0.1 µg/ml or 10 µg/ml histatin healed faster (shrunk more) at each of the time points where data was collected. These results are the first results of their kind done using in vivo animal studies.

Histatins and peptide portions or peptide fragments of histatins may be used to accelerate corneal wound healing or ocular surface disease healing in humans and other animals. In preferred embodiments, histatin 1 (Hst-1), histatin 2 (Hst-2), histatin 5 (Hst-5), peptide fragments of Hst1, Hst2, or Hst5, or any combinations thereof may be used. In other embodiments, histatin 3 (Hst-3) or the D-enantiomer of histatin 2 (D-Hst-2), or peptide fragments thereof, may be used. Any combinations of any of the histatins may be used. In preferred embodiments, histatin concentrations between 0.1 µg/ml and 1000 mg/ml may be used. Peptides with amino acid SEQ ID NOS: 1-33, histatins known in the art, the peptides disclosed in WO 2009/087117 or the peptides disclosed in Dr. Menno Johannes Oudhoff's thesis, "Discovery of the Wound-Healing Capacity of Salivary Histatins", 2010, department of Oral Biochemistry of the Academic Centre for Dentistry Amsterdam (ACTA), VU University Amsterdam and University of Amsterdam, The Netherlands, herein incorporated by reference, may be used.

In one preferred embodiment, histatin 1 (Hst-1) or histatin 2 (Hst-2) in combination with histatin 5 (Hst-5), peptide fragments of Hst-1 or Hst-2 in combination with peptide fragments of Hst-5, or any combination, are used. Hst-5 inhibits production of Matrix Metalloproteases (MMPs).

The combination of the Hst-1/Hst-2 healing properties with the Hst-5 inhibiting MMPs should be very effective. In some preferred embodiments, a concentration of at least approximately 1 µM of Hst-5, or a fragment of Hst-5, is used.

Histatins could be administered to humans or other animals with a corneal wound or ocular surface disorders. Some methods of administration include, but are not limited to, incorporating the histatin into eye drops, gels or ointments, incorporating the histatin into tissue glue used to transiently seal corneal injuries, or embedding the histatin into (polymer) contact lenses.

The histatins may be administered in any combination of daily treatments for any number of days in order to produce therapeutic results. In one preferred embodiment, the histatin is administered at least once a day for a plurality of days. In another preferred embodiment, the histatin is administered at least once a day chronically (for an extended period of time). In another preferred embodiment, the step may be repeated two, three, four, five times or more, or hourly, for a plurality of days or chronically. In one example, the histatin is repeated three times a day for seven days. In another example, histatin is administered four times a day for five days.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of treating ocular surface disease, comprising the step of administering a therapeutic amount of a composition comprising a first peptide and a second peptide to an ocular surface, wherein the first peptide comprises a first histatin or a fragment of the first histatin and the second peptide comprises a second histatin or a fragment of the second histatin;
    wherein the therapeutic amount of the composition is selected such that the composition accelerates healing of ocular surface disease compared to ocular surface disease not treated with the composition;
    wherein an amino acid sequence of each of the first peptide and the second peptide is selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; and any combination of SEQ ID NO: 1 through SEQ ID NO: 33;
    wherein the first peptide comprises the first histatin selected from the group consisting of: i) histatin 1 or a fragment of histatin 1, and ii) histatin 2 or a fragment of histatin 2; and
    wherein the second peptide comprises histatin 5 or a fragment of histatin 5.

2. The method of claim 1, comprising administering the composition using eye drops, gels, or ointments including the composition.

3. The method of claim 1, comprising administering the composition using tissue glue.

4. The method of claim 1, comprising continually administering the composition by incorporating the composition into a contact lens worn by a patient.

5. The method of claim 1, wherein the method treats humans.

6. The method of claim 1, wherein the concentration of each of the first peptide and the second peptide in the composition is between approximately 0.1 µg/ml and approximately 1000 mg/ml.

7. The method of claim 6, wherein the concentration of each of the first peptide and the second peptide in the composition is between approximately 0.1 µg/ml and 10 µg/ml.

8. The method of claim 1, further comprising repeating the step of administering the therapeutic amount of the composition to the ocular surface at least one time a day for a plurality of days.

9. The method of claim 1, further comprising chronically repeating the step of administering the therapeutic amount of the composition to the ocular surface at least one time a day.

10. The method of claim 1, further comprising repeating the step of administering the therapeutic amount of the composition to the ocular surface up to hourly for a plurality of days.

11. The method of claim 1, further comprising repeating the step of administering the therapeutic amount of the composition to the ocular surface at least two times a day for a plurality of days.

12. The method of claim 1, further comprising repeating the step of administering the therapeutic amount of the composition to the ocular surface at least three times a day for a plurality of days.

13. The method of claim 1, further comprising repeating the step of administering the therapeutic amount of the composition to the ocular surface three times a day for seven days.

14. The method of claim 1, further comprising repeating the step of administering the therapeutic amount of the composition to the ocular surface four times a day for five days.

15. The method of claim 1, wherein the first histatin in the first peptide is selected from the group consisting of:
   a) histatin 1; and
   b) histatin 2; and
      wherein the second histatin in the second peptide is histatin 5.

16. The method of claim 1, wherein the amino acid sequence of the second peptide is selected from the group consisting of SEQ ID NO: 30 and SEQ ID NO: 31.

17. The method of claim 1, wherein the amino acid sequence of the first peptide is selected from the group consisting of SEQ ID NO: 4; SEQ ID NO: 5; SEQ ID NO: 8; SEQ ID NO: 9; SEQ ID NO: 13; SEQ ID NO: 29; and SEQ ID NO: 33.

18. The method of claim 1, wherein the ocular surface disease is selected from the group consisting of dry eyes, corneal ulcerations and erosions, inflammatory and infectious keratitis and conjunctivitis, surgical interventions, and trauma.

19. The method of claim 1, wherein the first peptide and the second peptide are 8 to 44 amino acids in length.

20. The method of claim 1, wherein the first peptide and the second peptide are L-peptides.

21. The method of claim 1, wherein the first peptide is a cyclic peptide.

22. The method of claim 21, wherein the first peptide comprises SEQ ID NO: 33.

23. The method of claim 1, wherein the first peptide comprises SEQ ID NO: 33.

24. A method of treating ocular surface disease, comprising the step of administering a therapeutic amount of a composition comprising a first peptide and a second peptide to an ocular surface, wherein the first peptide comprises a first histatin or a fragment of the first histatin and the second peptide comprises a second histatin or a fragment of the second histatin;
   wherein the therapeutic amount of the composition is selected such that the composition accelerates healing of ocular surface disease compared to ocular surface disease not treated with the composition;
   wherein an amino acid sequence of each of the first peptide and the second peptide is selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; a variant amino acid sequence where one amino acid is substituted, deleted or inserted within at least one of the amino acid sequences of SEQ ID NOs: 1-33; and any combination of SEQ ID NO: 1 through SEQ ID NO: 33 and the variant amino acid sequences;
   wherein the first peptide comprises the first histatin selected from the group consisting of: i) histatin 1 or a fragment of histatin 1, and ii) histatin 2 or a fragment of histatin 2; and
   wherein the second peptide comprises histatin 5 or a fragment of histatin 5.

25. The method of claim 24, wherein the first peptide is a cyclic peptide.

* * * * *